United States Patent [19]
Christensen et al.

[11] 3,931,150
[45] Jan. 6, 1976

[54] PROBENECIDOXYMETHYL AND 1-ETHYL ESTERS OF AMPICILLIN

[75] Inventors: Burton G. Christensen, Scotch Plains; William J. Leanza, Berkeley Heights, both of N.J.

[73] Assignee: Merck & Co., Inc., Rahway, N.J.

[22] Filed: July 30, 1974

[21] Appl. No.: 492,654

[52] U.S. Cl............................. 260/239.1; 424/271
[51] Int. Cl.²...................................... C07D 499/68
[58] Field of Search................................ 260/239.1

[56] References Cited
UNITED STATES PATENTS
3,697,507  10/1972  Fredericksen et al..........  260/239.1

OTHER PUBLICATIONS
Remington's Pharmaceutical Sciences, 13th Ed., p. 1022 (1965).

*Primary Examiner*—Gerald A. Schwartz
*Attorney, Agent, or Firm*—Walter Patton; Julian S. Levitt; J. Jerome Behan

[57] ABSTRACT

New ampicillin derivatives, probenecidoxymethyl and 1-ethyl esters of ampicillin and their pharmaceutically acceptable salts, useful as antibiotics. A method for preparing these antibiotics by condensing probenecidoxymethyl or 1-ethyl halide with an acid salt of 6[D(-)-α-azidophenylacetamido] penicillanic acid, hydrogenating the azido group and isolating the product as a pharmaceutically acceptable salt of an acid. Pharmaceutical preparations containing the new antibiotics.

4 Claims, No Drawings

PROBENECIDOXYMETHYL AND 1-ETHYL ESTERS OF AMPICILLIN

BACKGROUND OF THE INVENTION

Free penicillins and their salts are generally less effective when taken orally than when administered parenterally. Because of inactivation in the stomach and gut, higher doses are required orally than parenterally in order to achieve the same blood levels, and there is a great variation in the ability of individuals to absorb penicillin into the blood by the oral route. Much research has in the past been directed to the discovery of penicillins which are less readily inactivated in the stomach and gut so that a relatively large part of the therapeutic agent administered orally can be absorbed into the blood. This has led to the development of some more highly orally-active penicillins.

When a penicillin arrives in the blood stream, whether by the oral or the parenteral route, some is broken down and the rest is excreted before inactivation. A dose of a sodium penicillin is normally completely eliminated from the body within a few hours of intramuscular injection. The concentration of the penicillin in the blood steadily decreases from its maximum level, and the pencillin may require replenishment by frequent repeated further administration in order to maintain a sufficient concentration until the presence of the therapeutic agent is no longer required. Accordingly research has in the past also been directed to the provision of long-acting preparations which release their penicillin content in such a way as to maintain a relatively high concentration of the therapeutic agent in the blood over a prolonged period. Thus, attempts have been made to solve this problem by means of penicillin salts or other derivatives from which the penicillin is chemically released in the body. It has in practice proved extremely difficult to find derivatives which will break down to release the free penicillin where it is required while at the same time not breaking down in the stomach. For example, many penicillin esters show no substantial therapeutic activity in man, as their hydrolysis to free penicillin in the body proceeds far too slowly.

Probenecid administered concomittantly with ampicillin derivatives has the valuable property of retarding the excretion of the ampicillin derivatives through the kidneys. The use of concomittantly administered probenecid for maintaining an elevated antibiotic level suffers from the disadvantage that several doses are required to build up the probenecid level so that its effect may be observed.

The present invention is directed to the new ampicillin derivatives, probenecidoxymethyl and 1-ethyl esters of ampicillin hydrochloride, which on oral administration are resistant to breakdown in the stomach but beyond the stomach hydrolyze with the release of free ampicillin which is absorbed and remains in the blood stream over a prolonged period by virtue of the fact that sufficient probenecid is formed as a result of the hydrolysis to retard the urinary excretion of ampicillin.

SUMMARY OF THE INVENTION

The ampicillin derivatives of the present invention are 6[D(−)-α-aminophenylacetamido] penicillanic acid (p-dipropylsufamoyl)benzoyloxymethyl and 1-ethyl esters having the structure:

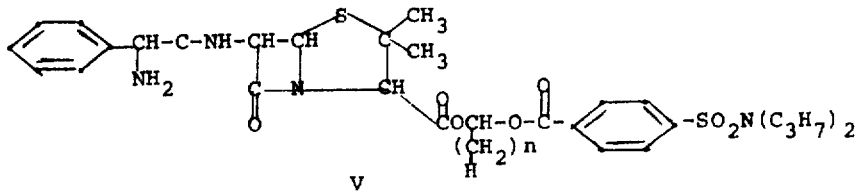

wherein $n=0$ or $1$, and their pharmaceutically acceptable nontoxic salts and hereinafter referred to as probenecidoxymethyl or 1-ethyl ester of ampicillin. Salts of the new esters may be formed with inorganic acids, e.g. hydrochloric, hydrobromic, hydriodic, sulfuric, and phosphoric and the like; and organic acids such as citric, tartaric, maleic acid, probenecid and the like. The preferred salt of the new esters is the hydrochloride.

A process for preparing the ampicillin derivative of the present invention is one in which a benzoyloxymethyl or 1-ethyl halide, wherein the halide is selected from the group consisting of chlorine, bromine and iodine, is caused to condense with an acid salt of 6[D(−)-α-azidophenylacetamido]penicillanic acid. Suitable acid salts are alkaline metal and amine salts, for example, lithium, sodium, potassium, tetrabutylammonium and triethyl amine salts. In the present invention the lithium salt is preferred. The benzoyloxymethyl or 1-ethyl halide is preferably the chloride but can also be the bromide or iodide. The benzoyloxymethyl or 1-ethyl chloride can be prepared by the reaction of benzoyl chloride with paraformaldehyde or acetaldehyde by heating the reagents together in the presence of anhydrous zinc chloride and subsequently isolating the benzoyloxymethyl or 1-ethyl chloride by column chromatography. The bromide or iodide can be prepared by reaction of the chloride with an alkali metal bromide or iodide in a suitable solvent.

The compound of the present invention is conveniently prepared by bringing the benzoyloxymethyl or 1-ethyl halide into contact with 6[D(−)-α-azidophenylacetamido]penicillanic acid salt in an inert solvent at a temperature within the range of from 0°–30°C. A suitable solvent for the reaction is dimethylformamide which, preferably, should be as dry as possible in order to avoid side reactions with water which reduce the yield of product. After the reagents have been allowed sufficient time to react the dimethylformamide is removed in vacuo. The residue is taken up in chloroform and the chloroform layer containing the product is washed with sodium bicarbonate and sodium chloride solutions. After drying and evaporating the chloroform solvent, the remaining residual oil is purified by column chromatography. The azido group of this product is converted to the amine by hydrogenation at 45 psi in the presence of platinum. The resulting amine is treated with an inorganic or organic acid to convert it into a non-toxic pharmaceutically acceptable salt. The probenecidoxymethyl or 1-ethyl ester of ampicillin hydrochloride salt, which is the preferred salt, is obtained by treating the probenecidoxymethyl or 1-ethyl ester of ampicillin with 1N hydrochloric acid and freeze-drying.

DESCRIPTION OF THE PREFERRED EMBODIMENTS

The process for preparing the ampicillin derivatives of the present invention is illustrated by the equations below wherein $n=0$ or 1.

The invention is illustrated by the following examples which illustrate the preparation of 6[D(−)-α-aminophenylacetamido]penicillanic acid p-(dipropylsulfamoyl)benzoyloxymethyl ester hydrochloride. One skilled in the art can apply these examples to prepare the corresponding 1-ethyl ester by merely substituted an equivalent amount of acetaldehyde for paraformaldehyde in Example 2. The infrared adsorption data (IR) refer to the positions of maxima given in reciprocal centimeters.

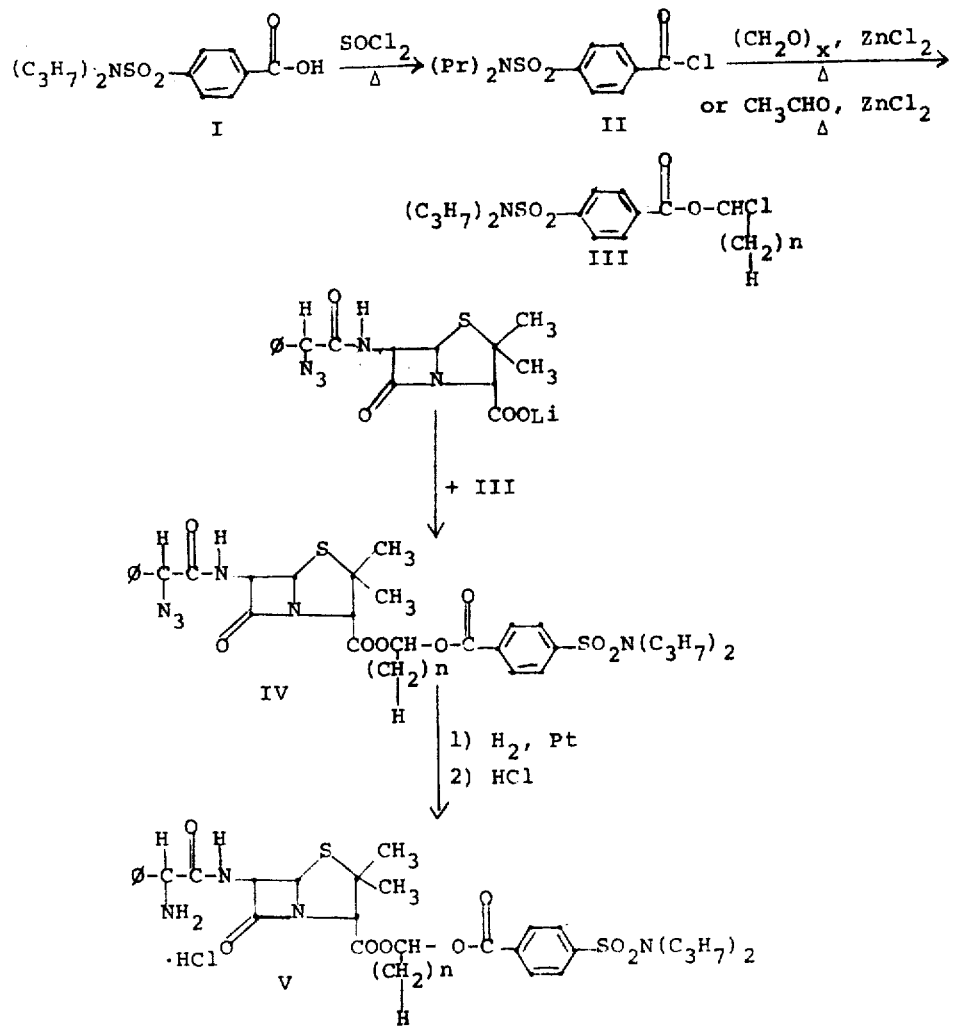

The process is one in which probenecid I is converted to its acid chloride II which is reacted with paraformaldehyde or acetaldehyde to give probenecidoxymethyl or 1-ethyl chloride III, respectively. The probenecidoxymethyl or 1-ethyl chloride III is reacted with the lithium salt of 6[D(−)-α-azidophenylacetamido]penicillanic acid to give 6[D(−)-α-azidophenylacetamido]penicillanic acid p-(dipropylsulfamoyl)benzoyloxymethyl or 1-ethyl ester which is hydrogenated to yield 6[D(−)-α-aminophenylacetamido]penicillanic acid p-(dipropylsulfamoyl)benzoyloxymethyl or 1-ethyl ester which is isolated as the hydrochloride salt. The 6[D(−)-α-azidophenylacetamido]penicillanic acid has been described in Belgian Pat. No. 620,519.

EXAMPLE 1

Preparation of p-(Dipropylsulfamoyl)benzoyl chloride II

To a suspension of 40 g. of p-(dipropylsulfamoyl)-benzoic acid (I) in 100 ml. of thionyl chloride is added 1 ml. of dry dimethyl formamide. The mixture is heated under gentle reflux for 18 hours and the thionyl chloride is removed under reduced pressure. The residual solid is extracted with hexane which is evaporated to give 40 g. of p-(dipropylsulfamoyl)benzoyl chloride (II) as a white solid m.p. 62°–63°C. I.R. 1750, 1785 cm$^{-1}$ (in nujol).

EXAMPLE 2

Preparation of p-(Dipropylsulfamoyl)benzoyloxymethyl chloride III

A mixture of 40 g. of p-(dipropylsulfamoyl)benzoyl chloride II, 40 g. of paraformaldehyde and 2 g. of freshly fuzed and powdered zinc chloride in 100 ml. of dry dioxane is heated with stirring at 95°–100°C. for 5 hours and allowed to cool. The mixture is extracted with ether which is decanted and washed with sodium bicarbonate solution and with saturated ammonium sulfate solution, then dried over magnesium sulfate, and evaporated. The residue is applied on a column packed with 500 g. of silica gel and the p-(dipropylsulfamoyl)benzoyloxymethyl chloride (III) recovered by elution with methylene chloride. The yield is 25 g. of a heavy oil which partially solidifies. I.R. (in nujol) shows a C=O band at 1750 cm$^{-1}$. In NMR, the CH$_2$Cl group appears as a singlet at 4.05$\tau$.

EXAMPLE 3

Preparation of 6[D(−)-α-azidophenylacetamido]penicillanic acid p-(dipropylsulfamoyl)benzoyloxymethyl ester IV A solution of 6[D-(−)-α-azidophenylacetamido]-pepenicillanic acid prepared by the method of Belgium Pat. No. 620,519, in ether is titrated with 0.2N lithium hydroxide to pH 7. The aqueous layer is separated and freeze-dried. To 8.1 g. of the lithium salt in 35 ml. of dimethylformamide is added 7 g. of p-(dipropylsulfamoyl)benzoyloxymethyl chloride and 3 g. of potassium iodide. The mixture is stirred at room temperature of six hours and the dimethylformamide is removed in vacuo. The residue is taken up in chloroform and washed with 3% sodium bicarbonate in 20% sodium chloride solution. The chloroform phase containing the product, is washed twice with sodium chloride solution, dried over sodium sulfate and evaporated. The residual oil is chromatographed on a column packed with 450 g. of silica gel. Preliminary portions are eluted with 9 l. of methylene chloride then the product 6[D(−)-α-azidophenylacetamido]penicillanic acid p-(dipropylsulfamoyl)benzoyloxymethyl ester (IV) is eluted with 1.5 l. of 5% ethylacetate in methylene chlordie. The yield of product is 3.5 g. TLC on silica gel in 5% ethyl acetate-methylene chloride gives a single spot at R$_f$ 0.4.

EXAMPLE 4

Preparation of 6[D(−)-α-aminophenylacetamido]penicillanic acid p-(dipropylsulfamoyl)benzoyloxymethyl ester hydrochloride V A solution of 3.7 g. of 6[D(−)-α-azidophenylacetamido]penicillanic acid p-(dipropylsulfamoyl)benzoyloxymethyl ester (IV) in 150 ml. of ethyl acetate is hydrogenated at a pressure of 45 psi in the presence of 1.5 g. of platinum oxide catalyst at room temperature for 90 minutes. The catalyst is filtered and ethyl acetate is evaporated under water-pump vacuum. The residual oil is dissolved in a mixture of 25 ml. of ethanol, 25 ml. of ethyl acetate and 15 ml. of water and brought to pH 3.0 by the addition of N hydrochloric acid, with vigorous stirring. The mixture is concentrated to about 20 ml.; 60 ml. of water is added and the mixture is extracted with 100 ml. of ether. The emulsion which is formed is separated by centrifugation and the aqueous layer is filtered and freeze-dried. The yield of 6[D(−)-α-aminophenylacetamido]penicillanic acid p-(dipropylsulfamoyl)benzoyloxymethyl ester hydrochloride (V) in the form of a white powder is 2.5 g. Paper electrophoresis at pH 7 gives a single band at the origin. Electrophoresis at pH 2 and 100 v/cm for 20 min. gives a single band with a mobility of −7 cm. The I.R. shows broad multiple bands at 1740–1800 cm$^{-1}$.

The present invention includes formulations in which the ampicillin derivatives of the invention are brought into association with pharmaceutically acceptable carriers to give a pharmaceutical formulations of the invention. The ampicillin derivatives of the present invention have the same usefulness as ampicillin in the treatment of humans and animals suffering from infections by pathogenic bacteria with the exception that whereas ampicillin is used in a dose range of from 200 mg. to 500 mg., the probenecidoxymethyl or 1-ethyl ester of ampicillin hydrochloride is preferably used in a range of 500 mg. to 1000 mg. because the molecular weight of the ester is approximately twice that of ampicillin. The ampicillin derivatives of this invention are useful in the treatment of infection in humans caused by the following pathogenic bacteria: various specie of *Enterococcus*, *Gonococcus*, *Meningococcus*, *Pneumonocuccus* and *Haemophilus influenzae*, *Proteus mirabilis*, α-and β-hemolytic *Streptococcus*. In animals the antibiotic of the present invention is useful in the treatment of infections caused by *Staphylococci*, *Streptococci* and *Escherichia coli*.

The pharmaceutical preparations of the invention for oral use comprise the probenecidoxymethyl and 1-ethyl esters of ampicillin and their pharmaceutically acceptable non-toxic salts in association with a pharmaceutically acceptable carrier suitable for oral administration.

The pharmaceutically acceptable carrier can be either solid or liquid. Solid form preparations include powders, tablets and dispersable granules, capsules and cachets. A solid carrier can be one or more substances which may also act as flavoring agents, solubilizers, lubricants, suspending agents, binders or tablet disintegrating agents. It can also be an encapsulation material. In powders the carrier is a finely divided solid which is in admixture with the finely divided compound. In tablets the suitable solid carriers are magnesium carbonate, magnesium stearate, and dextrins. Liquid form preparations include solutions and suspensions. Aqueous suspensions suitable for oral use can be made by dispersing the finely divided compound in water with sodium carboxymethyl cellulose as suspending agent.

Preferably the pharmaceutical preparation is in unit dosage form. In such form the preparation is subdivided in unit dosages containing appropriate quantities of the compound. The unit dosage form can be a package preparation, the package containing discrete quantities of preparation, for example, packeted powders. The unit dosage form can be a capsule or tablet itself or it can be the appropriate number of any of these in packaged form. A unit dose of the preparation may contain between 150 and 1,200 mg., and preferably from 500 to 1000 mg., of the penicillin derivative of the invention.

Below is described the method of formulating the probenecidoxymethyl and 1-ethyl esters of ampicillin hydrochloride with non-toxic, pharmaceutically acceptable carriers in the form of tablets, liquid preparations and capsules, the quantity of active ingredient being in the range between 150 and 1,200 mg., and preferably from 500 to 1000 mg. As a non-limiting example of a dosage unit, the formulation below describes the preparation of a tablet containing 500 mg. probenecidoxymethyl ester of ampicillin hydrochloride per tablet. One skilled in the art can use the Examples below to prepare formulations containing equivalent amounts of the corresponding 1-ethyl ester.

EXAMPLE 5

Tablets Containing Probenecidoxymethyl Ester of Ampicillin Hydrochloride:

EXAMPLE 5

Tablets Containing Probenecidoxymethyl Ester of Ampicillin Hydrochloride
Ingredients per 700 mg. tablet:

| | |
|---|---|
| Probenecidoxymethyl Ester of Ampicillin hydrochloride | 500 parts |
| Starch | 132 parts |
| Cellulose Powder | 60 parts |
| Magnesium Stearate | 6 parts |

The above ingredients are well mixed together, passed through a 140 screen, granulated and passed through a 60 screen. With the resulting granules there is mixed further magnesium stearate (1 part) and the mixture is then compounded in a tabletting machine, to give tablets of 700 mg. weight.

EXAMPLE 6

Liquid Preparation Containing probenecidoxymethyl Ester of Ampicillin Hydrochloride:

Probenecidoxymethyl ester of ampicillin hydrochloride is dissolved in polyethylene glycol of molecular weight 400 and the resulting solution diluted with the solvent in such a way that the final solution contains 100 mg./cc. of the ampicillin derivative. A suitable unit dose of the resulting liquid preparation of the invention is 5 cc.

EXAMPLE 7

Capsules Containing Probenecidoxymethyl Ester of Ampicillin Hydrochloride:

Solid probenecidoxymethyl ester of ampicillin hydrochloride is filled into gelatin capsules in quantities of 360 mg. per capsule, to give a solid preparation of the invention with the gelatin acting as pharmaceutical carrier.

The advantages of the invention are further illustrated by the following test results.

Ampicillin trihydrate and probenecidoxymethyl ester of ampicillin hydrochloride were given to beagle dogs to assess bioavailability. Probenecidoxymethyl ester of ampicillin hydrochloride was given to a group of four dogs, and the ampicillin trihydrate control to a group of six dogs. Ampicillin trihydrate was given in a dose of 23.1 mg./kg. and the probenecidoxymethyl ester of ampicillin in a dose of 39.1 mg./kg.

The dosages of each compound were based upon a level equivalent to 20 mg./kg. of anhydrous ampicillin. The compounds were given by gavage in a volume of 25 ml. of 1% aqueous methylcellulose; drug administration was immediately followed by a 15 ml. tap water flush of the gavage tube. Blood samples were collected in 5 ml. heparinized tubes just prior to treatment and 0.5, 1, 2, 3, 4, 6, 8, and 24 hours afterwards.

Food was withheld from the dogs for about 20 hours prior to dosing and throughout the first eight hours of sampling; a 400 gm. ration of commercial dog food (Wayne) was presented to the dogs after the eight-hour sample. Water was available at all times.

No physical signs, such as vomiting, diarrhea, etc., attributed to drug treatment were seen.

Ampicillin assay data are presented in Table I below.

TABLE I

Ampicillin Trihydrate - 23 mg./kg. initial dose - equal to 20 mg./kg. of anhydrous ampicillin

| | Hours After Administration | | | | | | | | | |
|---|---|---|---|---|---|---|---|---|---|---|
| | 0 | 0.5 | 1 | 2 | 3 | 4 | 6 | 8 | 24 | t ½ |
| Ampicillin - mcg./ml. plasma Average of six dogs | <0.13 | 4.19 | 6.64 | 5.00 | 2.23 | 0.90 | 0.17 | 0.03 | <0.13 | 0.8 hours |

Probenecidoxymethyl ester of ampicillin hydrochloride - 39.1 mg./kg. initial dose - equal to 20 mg./kg. of anhydrous ampicillin

| | Hours After Administration | | | | | | | | | |
|---|---|---|---|---|---|---|---|---|---|---|
| | 0 | 0.5 | 1 | 2 | 3 | 4 | 6 | 8 | 24 | t ½ |
| Ampicillin - mcg./ml. plasma Average of four dogs | <0.13 | 2.64 | 7.11 | 5.51 | 3.91 | 2.37 | 0.91 | 0.35 | <0.13 | 1.5 hours |

The results demonstrate the higher blood levels achieved with this compound of the invention after one hour and the prolonged maintenance of substantial levels for at least 8 hours, as compared to ampicillin trihydrate. Furthermore, the half life, $t$ ½, of ampicillin elimination was increased from 0.8 hours to 1.5 hours by the use of this compound of the invention. The half life, $t$ ½, is determined from the slope of a plot of $\mu g$ ampicillin/ml. plasma versus time in hours between 2 and 6 hours after administration of a test dose.

What is claimed is:

1. Probenecidoxymethyl ester of ampicillin or probenecidoxy-1-ethyl ester of ampicillin and non-toxic salts thereof.

2. A compound according to claim 1 wherein the non-toxic salt is the hydrochloride.

3. A compound according to claim 2 named probenecidoxymethyl ester of ampicillin hydrochloride.

4. A compound according to claim 2 named probenecidoxy-1-ethyl ester of ampicillin hydrochloride.

* * * * *